United States Patent [19]

Holtkamp, Sr.

[11] Patent Number: Plant 6,930

[45] Date of Patent: Jul. 18, 1989

[54] AFRICAN VIOLET PLANT NAMED LITTLE AMETHYST

[76] Inventor: Reinhold Holtkamp, Sr., Werther Strasse 112, D4294 Isselburg, Fed. Rep. of Germany

[21] Appl. No.: 192,680

[22] Filed: May 10, 1988

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner Schwartz, Jeffery Schwaab, Mack, Blumenthal & Evans

[57] ABSTRACT

A new and distinct cultivar of African violet named Little Amethyst characterized by its miniature growth habit; semi-double to double flowers having 8–12 petals, the ones in the center being much smaller and occasionally covering up the anthers; purplish red flowers with fine white edges; strong stems which curve toward the center to form a compact bouquet above the leaves; profuse and continuous flowering; very dark green, spear-shaped, serrated and very hairy leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Little Amethyst.

The new cultivar was referred to during the breeding and selection process by the designation I 485 and is a product of a planned breeding program. The new cultivar was originated from a cross made by me in the controlled breeding program in Haffen, Federal Republic of Germany. The female, or seed parent was a cultivar designated 4 Mini. The male, or pollen parent was a cultivar designated 69.

Little Amethyst was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Amethyst has not been observed under all possible environmental conditions. The phenotype may vary significantly with variations in environment such as temperature, light intensity and day length. The following observations, measurements and values describe the new cultivar as grown in a 4 cm pot in Haffen, West Germany and Nashville, Tenn. under greenhouse conditions which closely approximate those generally used in commercial practice.

The following traits have been repeatedly observed and are determined to be basic characteristics of Little Amethyst, which in combination distinguish this African violet as a new and distinct cultivar:

(1) Little Amethyst will not grow taller than 6–7 cm.
(2) Semi-double to double purplish red flowers with a fine white edge around the petals.
(3) Strong, wirelike and upright flowers stems curving toward the center.
(4) First flash of flowers forms a tight bouquet above the leaves.
(5) Profuse flowering; under good growing conditions continuous flowering.

(6) Each plant carries 7–8 and more upright flower stems each of which carries 5–7 and more flowers.
(7) Long lasting, non-dropping flowers.
(8) Plant saleable 10 to 11 weeks after planting of unrooted shoot.
(9) Seed capsules push slightly through.
(10) Very dark green, hairy leaves.
(11) Spear-shaped leaves are 2.0 to 3.5 cm in size.
(12) After maturity the flowers dry off, and remain on the peduncle.

The accompanying color photographic drawing shows a typical specimen plant of the new cultivar grown in a 4 cm pot. The plant is pictured on a hand to highlight the miniature size and growth habit of Little Amethyst. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 2 p.m. in Nashville, Tenn.

Botanical classification: *Saintpaulia ionantha,* Ramat, c.v. Little Amethyst.

Parentage:

*Male parent.*—69.

*Female parent.*—4 Mini.

Propagation: The new cultivar holds its distinguishing characteristics through successive propagations by leaf cuttings.

Plant: From 5.5 cm to 7 cm tall when grown in pots, and approximately 9–13 cm in diameter when fully grown.

*Leaves.*—General form: Spear-shaped. Diameter: 22–26 mm wide and 27–32 mm long. Texture: Velvety. Aspect: Serrated, very hairy, shiny. Veins: Upperside: visible; underside: well pronounced, light green, shiny; on young leaves purplish red. Color (upperside): Yellow-Green Group 147 A and darker. Color (underside): Greyed-Purple Group 183 between C and D. Petiole: Strong, purplish brown, hairy.

*Flowers.*—Buds: Size: 3–5 mm just before opening. Shape: Ball-shaped. Color: Purplish red, white petal edges visible. Sepals: Five (5). Color: Purplish brown. Calyx: Shape: Funnel-shaped. Aspect: Spear-shaped, hairy. Peduncle: Character: Strong upright, hairy. Color: Purplish brown. Individual flowers: Size: 20–24 mm. Shape: Semi-double to double; 8–12 petals per flower. Occasionally the 2–3 small petals in the center cover up the anthers. The young flowers look like a little rose. Color: (upperside): Purple Group 78 A; fine white line around edges. Under cooler temperatures and more intensive lighting, the purplish red tends to intensify. Color (underside): Purple Group 78 between A and B. Borne: Each flower stem carries 5–7 and more flowers on strong, upright peduncles that are free standing above the leaves, thereby forming a compact bouquet. Flowering habit: Flowers 10–11 weeks after planting an unrooted plantlet.

*Reproductive organs.*—Stamens: Two (2). Anthers: 2 composed of 4 anther cells, seed capsule pushes slightly through. Filaments: Yellowish green, 2 mm long. Styles: 4–5 mm long, purplish white, base of ovary light green and hairy.

*Roots.*—Normally developed, white when young, turning slightly brownish when older.

Disease resistance: Good.

General observations: Little Amethyst is a miniature violet, which does not grow taller than 6–7 cm and not larger than 9–13 cm. The semi-double to double flowers are composed of 8–12 petals, the ones in the center being much smaller and occasionally covering up the anthers. The petals are purplish red with a fine white edge. The flowers are long-lasting and non-dropping. The young flowers look like a little rose. Under good growing conditions Little Amethyst will bloom continuously. A nice bouquet of flowers free standing above the leaves develops approximately 10–11 weeks after planting an unrooted plantlet. Each of the 7–8 strong flower stems carries 5–7 and more flowers. The very dark green leaves are spear-shaped, serrated and very hairy.

I claim:

1. A new and distinct cultivar of African violet named Little Amethyst, as described and illustrated, and particularly characterized by its miniature growth habit; semi-double to double flowers having 8–12 petals, the ones in the center being much smaller and occasionally covering up the anthers; purplish red flowers with fine white edges; strong stems which curve toward the center to form a compact bouquet above the leaves; profuse and continuous flowering; very dark green, spear-shaped, serrated and very hairy leaves; flowering 10–11 weeks after planting of unrooted shoot, and by its long lasting and non-dropping flowers.

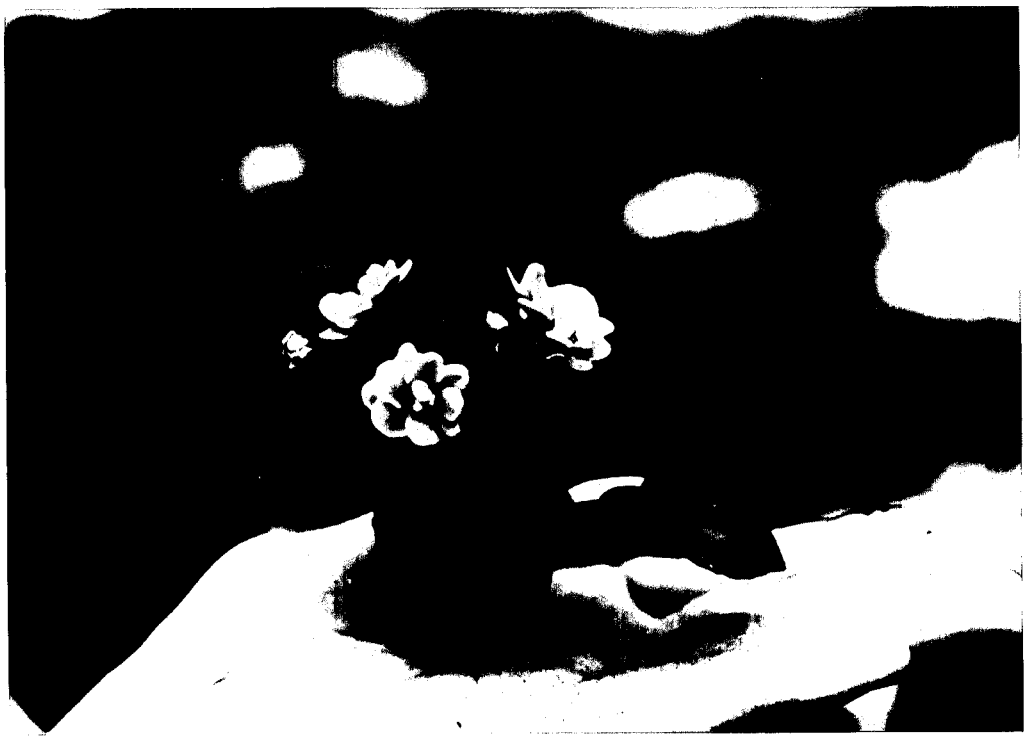

* * * * *